United States Patent [19]

Morgan et al.

[11] Patent Number: 5,834,780
[45] Date of Patent: Nov. 10, 1998

[54] SCANNING LINE SOURCE FOR GAMMA CAMERA

[75] Inventors: Hugh T. Morgan, Highland Heights; Gregory G. Cooley, Chardon; Bryce G. Thornton, Concord; Steven G. Plummer, Hudson, all of Ohio

[73] Assignee: Picker International, Inc., Highland Heights, Ohio

[21] Appl. No.: 654,542

[22] Filed: May 29, 1996

[51] Int. Cl.⁶ ............................ G01T 1/166; G01T 1/161
[52] U.S. Cl. .................................. 250/363.04; 250/498.1
[58] Field of Search ........................ 250/363.03, 363.04, 250/363.05, 363.07, 363.08, 497.1, 498.1

[56] References Cited

U.S. PATENT DOCUMENTS

| | | |
|---|---|---|
| 4,255,664 | 3/1981 | Rutt et al. . |
| 4,672,648 | 6/1987 | Mattson et al. . |
| 5,210,421 | 5/1993 | Gullberg et al. . |
| 5,479,021 | 12/1995 | Morgan et al. . |
| 5,552,606 | 9/1996 | Jones et al. ............... 250/363.04 |
| 5,576,545 | 11/1996 | Stoub et al. ............... 250/363.04 |

FOREIGN PATENT DOCUMENTS

| | | |
|---|---|---|
| 5892974 | 6/1983 | Japan . |
| 61235782 | 10/1986 | Japan . |

OTHER PUBLICATIONS

Larsson, et al.; "Simultaneous SPECT and CT with Shutter Controlled Radionuclide Sources and Parallel Collimator Geometry" IEEE Trans. Nuc. Sci.; vol. 40, No. 4, Aug. 1993, pp. 117–1122.

Tan, et al.; "A Scanning Line Source for Simultaneous Emission and Transmission Measurements in SPECT" The Journal of Nuc. Med., vol. 34, No. 10, Oct. 1993, pp. 1752–1760.

ADAC Laboratories Advertisment; Date Unknown.

U.S. Appl. Ser. No. 08/374,977; Plummer, et al.; filed Jan. 19, 1995; "Emission/Transmission Device for use with a Dual Head Nuclear Medicine Gamma Camera with the Transmission Source Located Behind the Collimator".

U.S. Appl. Ser. No. 08/483,276; Morgan, et al.; filed Jun. 7, 1995; "Gamma Camera Split Collimator Collimation Method and Apparatus".

Primary Examiner—Edward J. Glick
Attorney, Agent, or Firm—Timothy B. Gurin; John J. Fry

[57] ABSTRACT

A gamma camera system includes two or more radiation detector heads and which are mounted opposite each other to a gantry for rotation about a subject. A transmission radiation source assembly is mounted to the front face of at least one of the detectors and can be moved across the face of the detector. The source assembly includes a radiation attenuating housing, a leaded bronze source holder, and a radionuclide source. The radionuclide source is retained in a longitudinal groove disposed in the source holder. The source holder may be rotated into open, closed, and access positions. The transmission radiation emitted by the source assembly is directed across the examination region, attenuated by the subject, and detected by the opposed detector. The gamma camera system also includes a filter which selectively attenuates the transmission radiation based on the attenuation profile of the object so as to prevent saturation of the opposed detector. An image representation is reconstructed using the radiation emitted by the subject and corrected in accordance with the transmitted radiation data.

31 Claims, 5 Drawing Sheets

1

SCANNING LINE SOURCE FOR GAMMA CAMERA

BACKGROUND OF THE INVENTION

The present invention relates to the art of diagnostic imaging. It finds particular application in conjunction with single-photon emission computed tomography (SPECT) with single or multi-headed cameras and will be described with particular reference thereto. It is to be appreciated, however, that the invention will also find application in other nuclear medicine and transmission radiation diagnostic imagers.

Heretofore, single photon emission computed tomography has been used to study a radionuclide distribution in subjects. Typically, one or more radiopharmaceuticals are injected into a subject. The radiopharmaceuticals are commonly injected into the subject's blood stream for imaging the circulatory system or for imaging specific organs which absorb the injected radiopharmaceuticals. Gamma or scintillation camera heads are placed closely adjacent to a surface of the subject to monitor and record emitted radiation. In single photon-emission computed tomography, the head is rotated or indexed around the subject to monitor the emitted radiation from a plurality of directions. The monitored radiation data from the multiplicity of directions is reconstructed into a three dimensional image representation of the radiopharmaceutical distribution within the subject.

A drawback to the SPECT imaging technique is that the patient is not completely homogeneous in terms of radiation attenuation or scatter. Rather, the human patient includes many different tissue and bone types which absorb or scatter radiation from the radiopharmaceuticals to different degrees. The SPECT images can be made more accurate if they are corrected for the radiation lost to scattering or attenuation along each path through the human torso.

Accordingly, transmission radiation sources have been placed opposite the patient from a detector head. In three detector head systems, for example as disclosed in U.S. Pat. No. 5,479,021, which is commonly owned with the present application, the fan beam radiation source is mounted to the rotating gantry between two of the detectors and opposite the third. Such a mounting arrangement is of course not applicable to opposed, two detector head systems.

In single head systems, for example as disclosed in Tan, *A Scanning Line Source for Simultaneous Emission and Transmission Measurements in SPECT*, J. Nuclear Med., Vol. 34, No. 10, Pg. 1752 (October 1993) a scanning line source is mounted on a frame attached to the collimator of the single head. This technique is also inapplicable to opposed two headed systems, particularly in light of the of the line source's height, the need to provide effective shielding between the line source and the second detector while reducing the effective height of the source assembly, the limitations imposed by the frame, and the inability to adjust the relative distances between the transmission source, the object being imaged, and the detector.

Scanning line sources have also been used in two head right angle systems wherein the detectors are mounted at a 90° angle to each other. In such a system, however, close body orbits are problematic because one head can get in the way of the other and the patient is not centered in the field of view. Accordingly, it is desirable to apply a line source in a system having opposed detectors.

One technique for transmission imaging in an opposed detector system is to mount the line source at the side of one of the opposed detectors. A significant drawback to this approach is that the collimator of the opposed detector must be modified to allow detection of the transmitted radiation, which can increase patient to detector distance and adversely affect resolution and image quality. Such a modification has a deleterious effect on the detector's field of view.

Yet another drawback to the prior art line source techniques is that radiation emitted by the line source but not attenuated by the subject reaches the detector without substantial attenuation. This "shine by" radiation results in extraneous detector counts and can cause saturation of the detector, leading to inaccuracies in the image data.

The present invention contemplates a new and improved scanning line source which is particularly suited to two headed gamma cameras and other gamma cameras having opposed detector heads. The present invention further contemplates a technique for shaping the intensity of the transmitted radiation so as to reduce the undesirable effects of shine by radiation. As described more fully below, present invention overcomes the above-referenced problems and others.

SUMMARY

A new and improved scanning line source method and apparatus for a SPECT or nuclear camera is provided. A gantry movably supports a pair of opposed detector heads for movement around an examination region. The detector heads receive radiation from the examination region and generate data indicative of the received radiation. A transmission radiation source is movably mounted between the first detector and the examination region, and across the examination region from the second detector head. The invention also includes means for moving the source across the face of the first detector. The second detector is thus selectively irradiated by transmission radiation from the first transmission radiation source.

According to another aspect of the invention, the radiation source includes a housing, a source holder mounted within the source housing, and a radionuclide source retained by the source holder. The radionuclide source is offset from the center of the source holder.

According to another aspect of the invention, the system includes means for disposing the radionuclide source in an open, a closed, and an access position.

A second transmission radiation source may also be provided, the second transmission radiation source being movably mounted between the radiation sensitive face of the second detector head and the examination region and across the examination region from the first detector head. The system comprises means for moving the second radiation source across the face of the second detector head such that the first detector head is selectively irradiated by transmission radiation.

According to another aspect of the invention, the invention comprises means for selectively locking the source assembly in position and releasing the source assembly such that the source assembly is selectively removable.

According to another aspect, the invention comprises a means for varying the intensity of the transmission radiation according to a desired intensity profile. In particular, the intensity of the transmitting radiation is generally related to the attenuating characteristics of an object situated in the examination region.

One advantage of the present invention is that accurate transmission radiation correction may be obtained with an opposed dual head gamma camera. Another advantage of the present invention is that the scanning line source presents a low profile such that the radiation detector faces may be disposed near the patient. Yet another advantage of the present invention is that access to the radionuclide source is facilitated. Yet another advantage is that spurious transmission radiation counts in the detector behind the line source are reduced.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 5 depicts a top perspective view of a transmission collimator according to the present invention.

FIG. 7 is a detail view of radionuclide source retaining clips according to the present invention.

DETAILED DESCRIPTION

Figure 1:
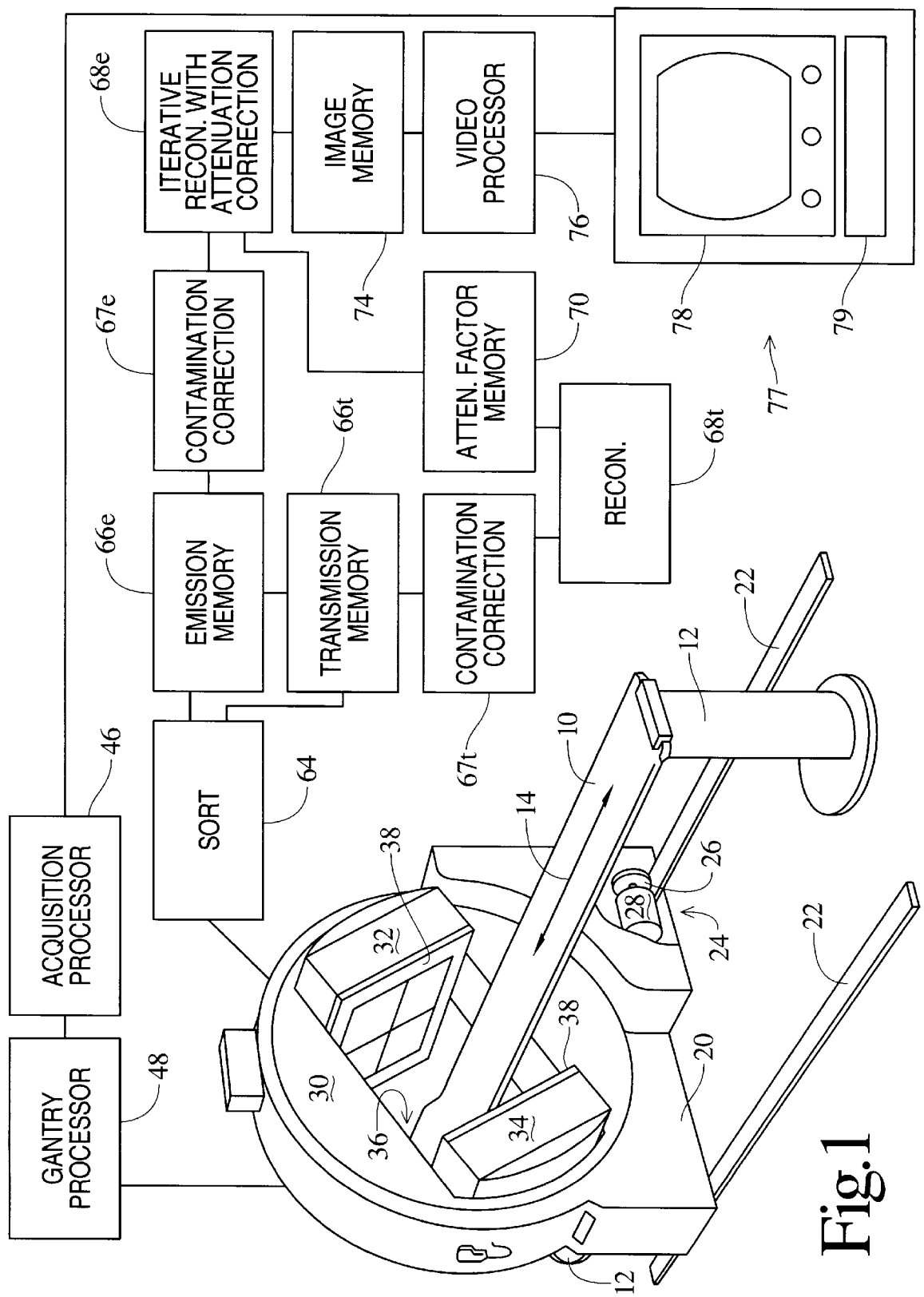
FIG. 1 is a perspective view of a gamma camera system in accordance with the present invention.

With reference to FIG. 1, a subject support or table 10 is mounted to stationary, vertical supports 12 at opposite ends. The subject table is selectively positionable up and down to center the subject in the center of a circle along a longitudinal axis 14.

An outer gantry structure 20 is movably mounted on tracks 22 which extend parallel to the longitudinal axis. This enables the outer gantry structure to be moved parallel to the longitudinal axis 14. An outer gantry structure moving means 24 is provided for selectively moving the outer gantry structure 20 along the rails 22 in a path parallel to the longitudinal axis. In the illustrated embodiment, the longitudinal moving means includes drive wheels 26 for supporting the outer gantry structure on the tracks. A motive power source, such as a motor 28, selectively drives one of the wheels which frictionally engages the track and drives the outer gantry structure and supported inner gantry structure and detector heads therealong. Alternately, the outer gantry can be stationary and the subject support configured to move the subject along the longitudinal axis.

An inner gantry structure 30 is rotatably mounted on the outer gantry structure 20. A first camera or detector head 32 is movably mounted to the inner gantry structure. A second detector head 34 is movably mounted to the inner gantry structure opposite to the first camera head. The detector heads are independently movable toward and away from each other. The inner gantry structure defines a central, subject receiving aperture 36 for receiving the subject table and permitting relative movement with respect to the patient, particularly along the longitudinal axis. The aperture 36 is enlarged to receive the detector heads in any of a variety of displacements from a central axis and angular orientations.

The detector heads have collimators 38 to restrict received radiation to radiation traveling generally perpendicular to the detector faces. The detector heads also include a scintillation crystal that emits a flash of light in response to incident radiation and an array of photomultiplier tubes which converts the light into electrical signals. A resolver circuit resolves the x, y-coordinates of each light flash and the energy of the incident radiation.

Figure 2:
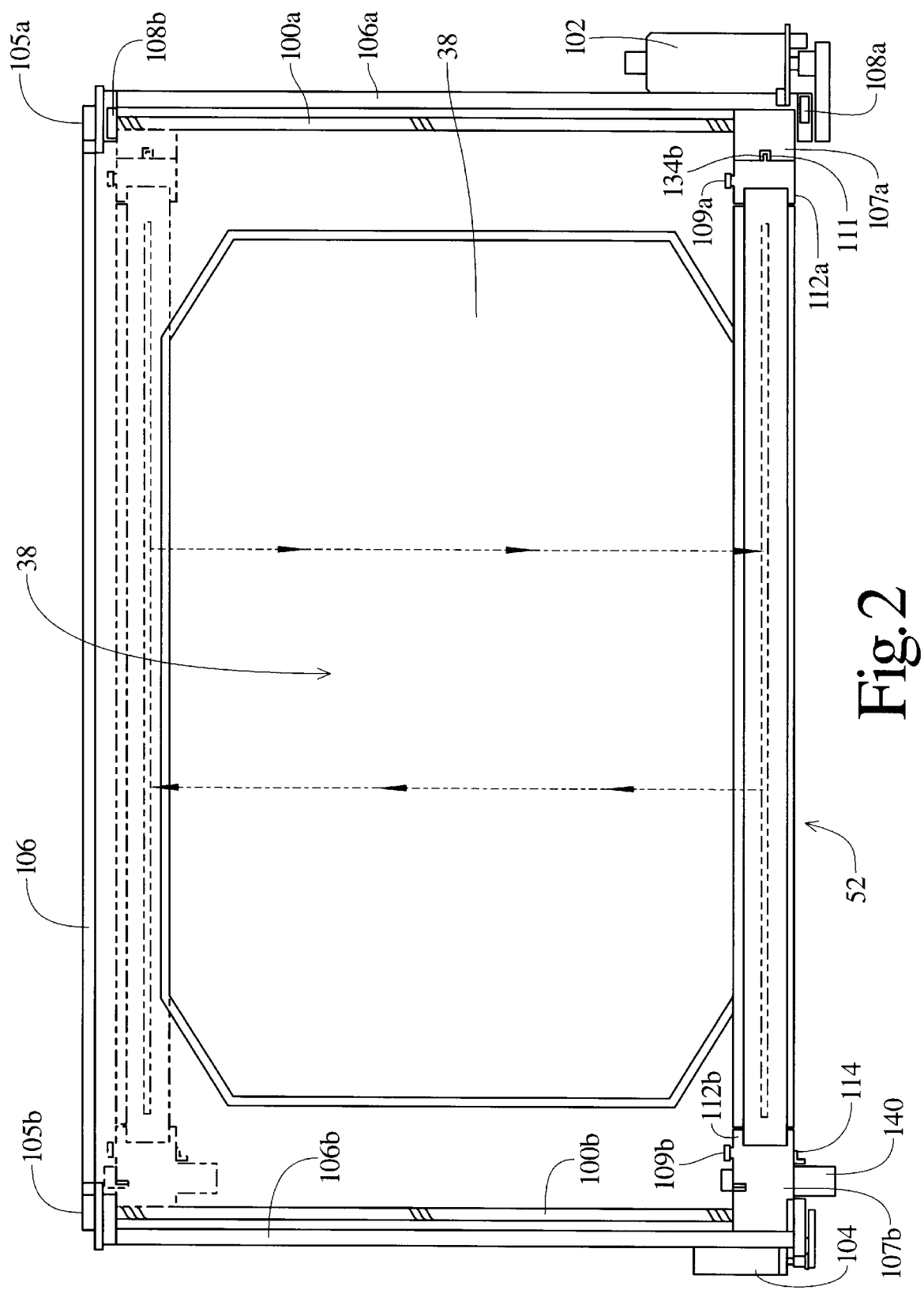
FIG. 2 is a front view of a detector and scanning line source according to the present invention.

With reference to FIG. 2, a transmission radiation source assembly 52 is disposed along the front surface of the collimator 38. Preferably, the radiation source assembly 52 is a line source extending across the collimator 38 in a direction substantially orthogonal to the longitudinal axis 14. The direction of motion is depicted by the arrows in FIG. 2; the source assembly 2 is shown in two representative positions. A drive mechanism moves the radiation source assembly 52 across the front of the collimator in the direction of the longitudinal axis 14. The transmission radiation source assembly 52 may also be mounted between the scintillation crystal and the collimator 38, or between the sections of a collimator having two or more sections. During operation, the collimator 38 and source assembly 52 are behind a cover and are thus hidden from view.

The source assembly 52 is driven by a DC motor 102 connected to acme screw drive assemblies 100a and 100b. The position and speed of the source assembly is sensed using an optical encoder integral to the DC motor 102 and a potentiometer 104. This information is used by the gantry processor 38 to provide closed loop control of the source assembly's position and speed. The gantry processor 38, power supplies, motor driver, and associated electronics are mounted in the rotating portion of the gantry 30. A cable carries signal and power to the drive components on the collimator 38.

The drive screw assemblies 100a and 100b are mounted on drive block support rails 104a and 104b. The support rails 104a and 104b are in turn mounted on the collimator 38. A timing belt transfers motive power from the drive screw assembly 100a to the drive screw assembly 100b via the pulleys 105a and 105b. Limit switches 108a and 108b provide a definitive indication of source assembly 52 position and establish end of travel limits. The potentiometer 104 provides an independent indication of drive screw 100b motion which is used to verify that drives screws 100a and 100b remain synchronized.

Figure 3:
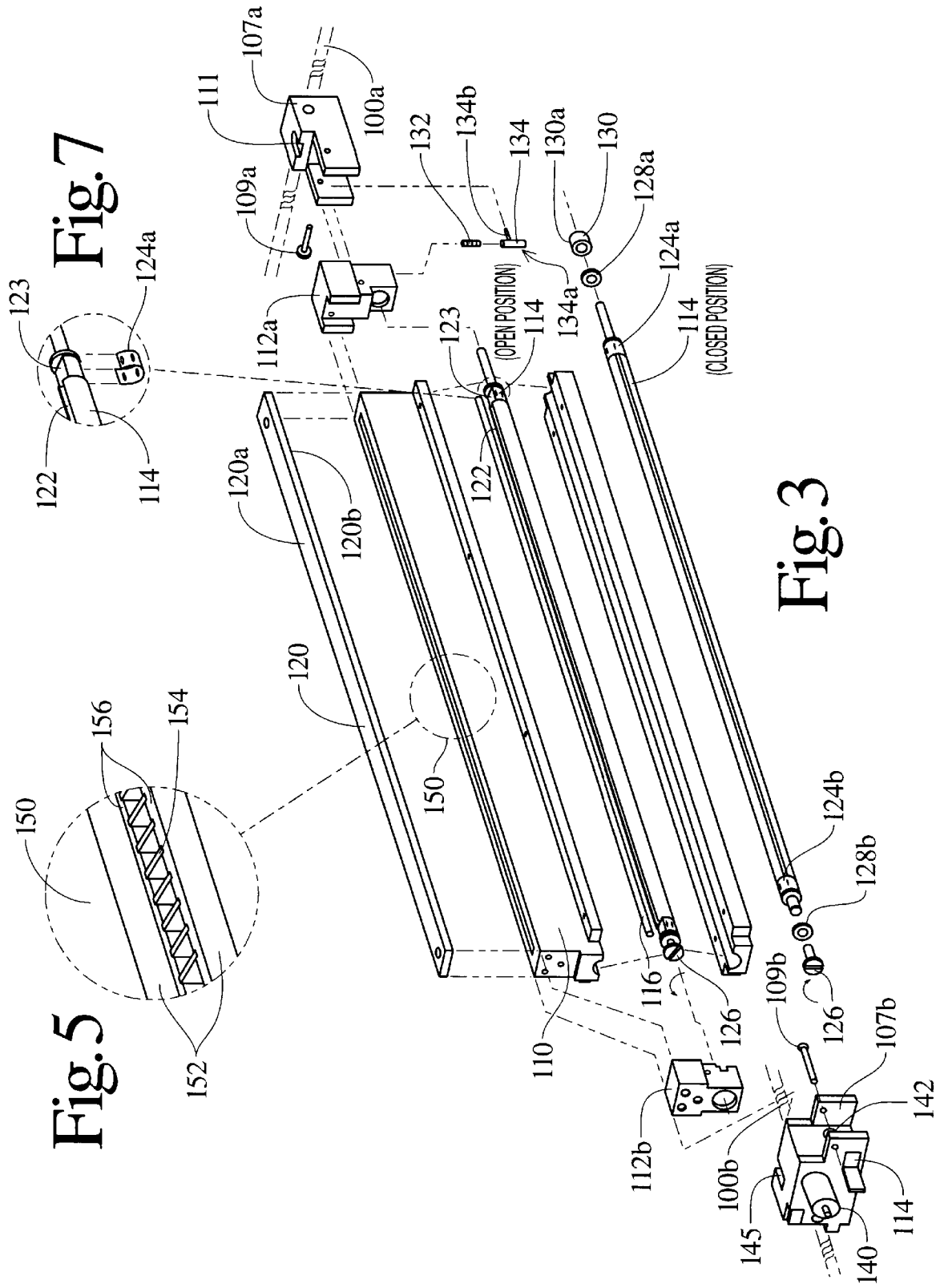
FIG. 3 is an exploded view of a scanning line source according to the present invention.

Drive blocks 107a and 107b engage the acme screws 100a and 100b. The radiation source assembly 52 is removably fastened to the drive blocks 107a and 107b using fasteners 109a and 109b such as pins, screws, clips, or the like which engage complementary apertures in the source assembly 52 and the drive blocks 107a and 107b. With reference to FIG. 3, bearing blocks 112a and 112b slidably engage within cavities defined by each of the drive blocks 107a and 107b.

Hence, the source assembly 52 is inserted and removed from the drive blocks 107a and 107b in a direction perpendicular to the face of the collimator 38.

With reference to FIG. 3, the radiation source assembly 52 comprises a housing 110, source holder 114, radionuclide source 116, bottom cap 118, filter assembly 120, and bearing blocks 112a and 112b.

Figure 4:
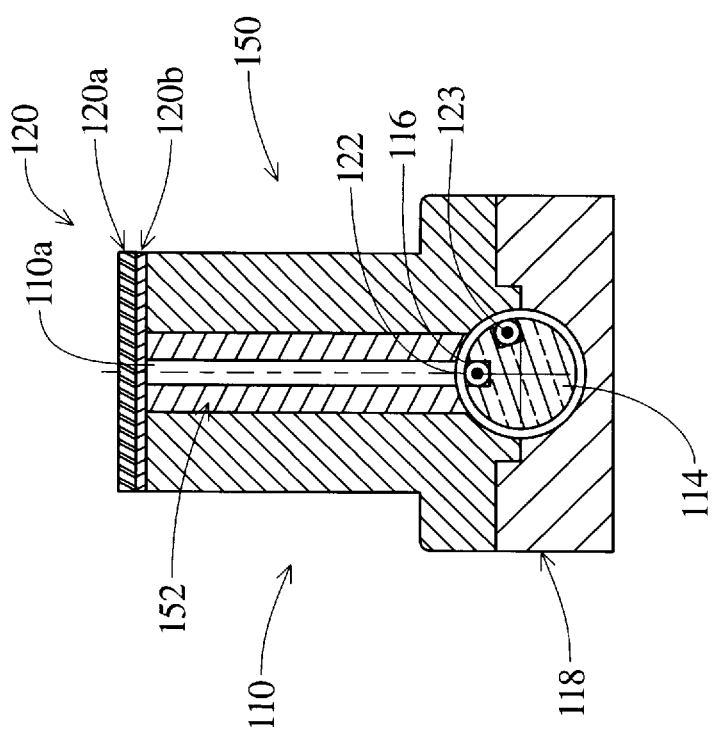
FIG. 4 is a side view depicting a cross section of a scanning line source according to the present invention.

With reference again to FIGS. 4 and 5, the housing further includes a transmission radiation source collimator 150. The transmission collimator means 150 includes a pair of substantially parallel lead side walls 152. A plurality of thin septa 154 are mounted between the 30 side walls 152. The septa 154 are constructed of a material which has good radiation stopping power and which, when struck by radiation, emits a gamma ray of relatively low energy, e.g., below 50 keV. Preferably, the septa 154 are constructed of tin or any alloy of tin and antimony. Tin emits gamma rays with a characteristic energy of about 30 keV. Other suitable materials for the septa include metals with an atomic number of about 30–70, particularly tin, antimony, zirconium, niobium, molybdenum germanium, yttrium, cerium, gadolinium, terbium, dysprosium, holmium, erbium, ruthenium, rhodium, palladium, silver, cadmium, indium, tellurium, cesium, barium, and alloys thereof. Of these, tin, antimony, molybdenum, zirconium, and cadmium are preferred for their more ready availability. The side walls of the collimator 152 could also be made of such materials. However, because many scans call for placing the detector heads as closely adjacent as possible, the transmission radiation source and collimator preferably have as narrow a profile as possible. To this end, the greater stopping power of lead, or other high atomic number material, which permits the radiation source assembly to be as small as possible is preferred. It will be noted that the surface area of the septa which are exposed to radiation from the line source is many times greater than the surface area of the side walls. Optionally, the side walls may be covered or plated on their exposed inside surfaces with tin or one of the other above-discussed metals to limit the emission of the 72 keV to 88 keV characteristic x-rays of lead.

The source holder 114 is preferably a cylindrical rod having a diameter of approximately 0.291 inches (7.4 mm). The source holder 114 contains a longitudinal groove 122 having a length, width, and depth sufficient to accommodate the radiation source. A depth of approximately 0.102 inches (2.6 mm) and a width of approximately 0.089 inches (2.3 mm) is suitable. The groove 122 has a generally rectangular cross section. The source holder 114 optionally but preferably comprises a further generally rectangular longitudinal groove 123 offset from the source holder groove 122 by about 75°. The rectangular groove 123 contains a radiation attenuating material such as tin, the depth and width of the groove and the attenuating material being selected to provide a desired radiation attenuation. The source holder 114 is comprised of a material which provides a desired degree of radiation attenuation, is relatively easy to machine, and exhibits sufficient structural rigidity. A suitable material is, for example, a high leaded tin bronze containing 81%–85% copper, 6.3%–7.5% tin, 6.0%–8.0% lead, 2.0%–4.0% zinc, 0.2% iron, 0.35% Sb, 1.0% Nickel, 0.8% sulfur, 0.15% P, 0.005% aluminum, and 0.005% silicon.

The diameter of the source holder 114 is reduced near the ends of the radionuclide source 116 to accommodate radionuclide source retaining clips 124a and 124b. The depth and width of the groove 122 are also increased near the ends of the radionuclide source 116 so that the radionuclide source 116 may be more readily gripped with a tool. To this end, the cross section of the groove 122 in this region is also generally trapezoidal with the larger dimension disposed at the outer edge of the source holder 114.

A slotted drive spindle 126 and ball bearing assembly 128a are affixed to the drive end of the source holder 114. A ball bearing assembly 128b and a locking disc 130 are affixed to the other end. The drive spindle 126, bearings 128a and 128b, and locking disc 130 define an axis of rotation about the center of the source holder 114.

The radionuclide source 116 is a cylindrical rod with a diameter slightly less than the width of the slot, for example, about 0.086 inches (2.2 mm). When inserted into the groove 122, the radionuclide source 116 is retained near to the periphery or outer edge of the source holder 114. Stated another way, the radionuclide source 116 is offset from the center of the source holder 114. The radionuclide source is also substantially offset from the source holder 114 axis of rotation. The radionuclide source 116 is, for example, a sealed steel tube containing a source such as Gd-153, Tc-99m, Co-57, or others.

The bottom cap 118 mates to the housing 110 and is removably fastened thereto using fasteners such as screws, clips, or the like. When mated, the bottom cap 118 and housing 110 define a cylindrical bore for receiving the source holder 114. The bottom cap 118 is a radiation attenuating material such as lead.

The filter 120 extends across an outlet aperture 120 of the transmission collimator 150 and is fastened thereto using fasteners such as screws. The filter 120 includes an inner layer 120b of a material which stops substantially all of the 72 keV to 88 keV energy x-rays from the lead in the side walls 152 of the transmission collimator, yet passes a substantial portion of the radiation from the transmission line source 116. The filter 120 further includes an outer layer 120a which stops substantially all of the lower energy radiation emitted by the inner layer 120b and by the septa 154. In the preferred embodiments in which the septa are tin or tin/antimony alloy, the inner layer 120b is also tin or tin/antimony and the outer layer 120a is aluminum. The aluminum not only absorbs gamma rays in the 30 keV range, but provided structural strength to the softer tin. Of course, the same alternate metals which can be used to construct the septa can also be used for the inner filter.

Optionally but preferably, a third filter layer is comprised of the same material as first layer is disposed at the output of the transmission collimator 150 upstream from the filter 120. The total thickness of the inner layer 120b and the third layer is adjusted to provide a desired attenuation.

Bearing block assemblies 112a and 112b are fastened to the housing 110 using fasteners such as screws, clips, or the like. The bearing blocks define apertures for receiving the ball bearing assemblies 128a and 128b. The bearing blocks 112a and 112b are preferably bronze.

Bearing block assembly 112a further comprises a spring 132 and a locking pin 134. The spring 132 urges the locking pin in the direction of the locking disc 130. A first protrusion or member 134a engages a radial aperture 130a in the locking disk 130. Hence, in a first position, the locking pin prevents the source holder 114 from rotating. A second protrusion or member 134b extends through a vertical slot (not shown) in the bearing block 112a When the source assembly 52 is mounted on the collimator assembly 38, the second member 134b engages a groove 111 on the drive block 118, thereby urging the locking pin 134 against the spring. When in this second position, the first member 134a is no longer engaged in the locking disc 130. Hence, the locking pin 134 does not prevent rotation of the source holder 114.

With further reference to FIG. 3, the drive block assembly 107b further comprises an actuating solenoid 140, a mechanical linkage arrangement including a return spring (not shown), a rotate spindle 142, and a position sensor 144. The linkage includes a flag (145) which permits the position of the linkage and thus the source holder 114 to be ascertained visually and further permits manual positioning of the linkage.

The rotate spindle 142 includes a protrusion for engaging the slot on the drive spindle 126 when the source assembly 52 is installed on the collimator 38. When energized, the solenoid 140 engages the linkage arrangement, which converts the linear motion of the solenoid 140 into rotational motion and causes the rotate spindle 142 to rotate approximately 75°. The source holder 114 is thus rotated to a first or open position. When the solenoid is de-energized, the return spring causes the shutter rotate spindle 142 and hence the source holder 114 to rotate approximately 75° and return to the second or closed position. Position sensor 144 is used to confirm the actual position of the source holder 114.

Prior to installation of the source assembly 52 on the collimator 38, the locking pin 134 engages the locking disc 130. With reference to FIG. 3, the aperture 130a on the locking disc 130 and the groove 122 on the source holder are offset by about 75°. The radiation source 116 is thus locked in a position facing the side of the source housing 110. In this closed position, the radiation emitted by the source 116 is absorbed by the housing 110 and the source holder 114. The groove 123 is also generally aligned with the collimator slot 110a so that the radiation attenuating material contained in the groove 123 provides additional shielding against radiation emission through the collimator. The slot in the drive spindle 126 and the source holder groove 122 are likewise offset by about 75°. In the closed position, the slot on the shutter coupling 126 is therefore vertical. When the solenoid is de-energized, the protrusion in the shutter rotate spindle 142 is likewise vertical.

The source assembly 52 is installed on the collimator 38 by slidably engaging the bearing blocks 112a and 112b with the drive block 107a and 107b. The drive spindle 126 slot and the rotate spindle 142 protrusion, both being vertical, likewise slidably engage. The first pin 134b on the locking pin 134 likes engages the groove 111 on the drive block 107a such that the second pin 134a on the locking pin 134 no longer engages the locking disc 130. The source holder 114 is thus free to rotate in response to rotation of the shutter rotate spindle 142. The fasteners 109a and 109b hold the source assembly 52 in place.

When energized, the solenoid 140 causes the rotate spindle 142, and hence the source holder 114 to rotate approximately 75° to the open position such that the radionuclide source 116 faces the transmission collimator 150. Hence, radiation emitted by the source 116 is emitted from the source assembly 52 through the examination region in the direction of the opposite detector. Because the rotate spindle 142 protrusion and the drive spindle 126 slot are approximately 75° from the vertical, the source assembly 52 cannot be removed from the drive blocks 107a and 107b while the source holder is in the open position.

When in the open position, the source holder 114 presents a substantial attenuation path between the radionuclide source 116 and the bottom cap 118. Hence, the source holder 114 presents a significantly greater attenuation path compared to source holders where the radionuclide source is located centrally. This increased attenuation path length provides increased design flexibility by allowing, for example, a reduction in the source assembly height, a reduction in source holder diameter, easier access to the radionuclide source, and construction of the source holder using a material having lesser radiation attenuating properties, while providing acceptable shielding between the radionuclide source and the detector to which the source is attached.

When the solenoid 140 is de-energized, the spring causes the shutter rotate spindle 142, and thus the source holder 114, to rotate approximately 75° back to the closed position. If desired, the source assembly 52 can again be removed from the collimator 38.

The radionuclide source 116 is replaced with the source assembly removed from the collimator 38. The bottom cap 118 is removed from the source housing 110 to permit access to the source holder 114. The second member 134b on the actuator pin 134 is depressed to permit rotation of the source holder 114, and the source holder 114 is rotated until the radionuclide source 116 is accessible. The second member 134b is then released such that first member 134b engages a second radial aperture (not shown) on the locking disc 130. The source holder 114 is thus locked in a third or source access position. The source retention clips 124a and 124b are rotated until slots disposed therein coincide with the radionuclide source, and the radionuclide source 116 is removed. The new radionuclide source 116 is installed and the retention clips 124a and 124b are rotated so that the radionuclide source 116 is again held in place. The first pin 134a is again depressed and the source holder 114 is manually rotated to the closed position. The first pin 134a is released such that the source holder 114 is locked in the closed position. The bottom cap 118 is reinstalled. The source assembly 52 can now be reinstalled.

Conventional gamma detector heads image radiation in two or more energy windows or ranges simultaneously. In a conventional dual energy gamma detector head, the signals are sorted based on amplitude. More specifically, energy windows or ranges are defined. Each window corresponds to a photopeak or energy spectrum of a radionuclide to be used in the examination. When using a radiation source 52, the injected or emission radionuclide has one preselected energy and the radiation source 52 or transmissive radiation has a second, different energy. In this manner, the detector heads 32 and 34 separate the transmission and emission radiation data by using the conventional energy separation circuitry used during dual injected radiopharmaceutical examinations. A position resolver (not shown) resolves the position on the crystal corresponding to scintillations or radiation events within each of the energy windows.

During a scanning operation, the collimator 38 of the preferred embodiment limits the emission and transmission radiation received by the detector face to radiation travelling generally perpendicular to the face. The non-perpendicular radiation is primarily absorbed by the collimator walls. Concurrently, the radiation source assembly 52 is moved across the face of the opposed detector by the drive mechanism. The transmission radiation from the radiation source 52 is also restricted by its associated collimator 150 such that only radiation that is substantially parallel to the collimator is allowed to pass through the collimator towards the subject. Thus, radiation which is not useful in creating a transmission image is prevented from being transmitted and absorbed by the subject. The transmission radiation from the radiation source 52 enters the subject and is attenuated by the subject and received by the opposite detector. The transmission radiation received by the opposite detector is used to create transmission projection data.

With reference again to FIG. 1, a reconstruction technique for emission and transmission data is provided. Of course, the reconstruction technique changes according to the types of radiation collected and the types of collimators used (i.e., fan, cone, parallel beam). Emission radiation from the subject is received by both detector heads 32 and 34 and emission projection data is generated. The emission data normally contains inaccuracies caused by varying absorption characteristics of the subject's anatomy. A sorter 64 sorts the emission projection data and transmission projection data on the basis of the relative energies. The data are stored in a projection view memory 66, more specifically in corresponding emission data memory 66e and transmission data memory 66t. Contamination correction 67e is applied to the emission data to correct for emission counts attributable to transmission radiation such as my be caused by scatter or varying composition of the transmission radionuclide source. Contamination correction 67t is similarly applied to the transmission data to correct for transmission counts attributable to emission radiation such as my be caused by scatter or varying composition of the emission radionuclide source. A reconstruction processor 68t reconstructs the transmission data into a transmission image representation or volume of attenuation factors stored in a memory 70. Each voxel value stored in the memory 70 is indicative of attenuation of tissue in a corresponding location within the patient. An iterative reconstruction algorithm 68e reconstructs the emission data and also corrects the reconstructed image based on the attenuation factors contained in the attenuation correction factor memory 70. The reconstructed image representation is stored in a volumetric image memory 74. A video processor 76 withdraws selected portions of the data from the image memory 74 to generate corresponding human-readable displays on a video monitor 78. Typical displays include reprojections, selected slices or planes, surface renderings, and the like.

An operator control panel 77 includes a video monitor 78 for converting selected portions of the emission image representation into a human readable display. Optionally, transmission images might also be displayed. A keyboard 79 enables the operator to control the image reconstruction process, the selection of displayed data, the selection of preselected scanning procedures, and custom operation of the SPECT camera gantry. That is, the operator can control rotation of the rotatable gantry portion 30, movement of the detector heads 32, 34 radially toward and away from the examination region 36, positioning the patient couch 10, and the position of the line source assembly 52. The distance between each of the detectors 32 and 34 may also be independently adjusted. In particular, it is desirable that each detector head 32 be placed as close to the subject as possible.

It is also desirable to limit the radiation emitted by the source assembly 52 based on the dimensions and the attenuation characteristics of the object being imaged. Radiation from the transmission source assembly 52 traverses the examination region 36 and impinges on the opposing detector 32 or 34. Inasmuch as the object being imaged does not ordinarily fill the entirety of the imaging region 36, some of the transmitted radiation reaches the opposing detector without substantial attenuation. This unattenuated "shine by" radiation may be of sufficient intensity to saturate the detector, thereby distorting the images and attenuation measurements produced by the system. Accordingly, the intensity of the radiation transmitted by the source assembly is preferably varied in a manner generally inverse to the attenuating characteristics of the object being imaged such that detector counts attributable to the "shine by" radiation are reduced.

Figure 6:
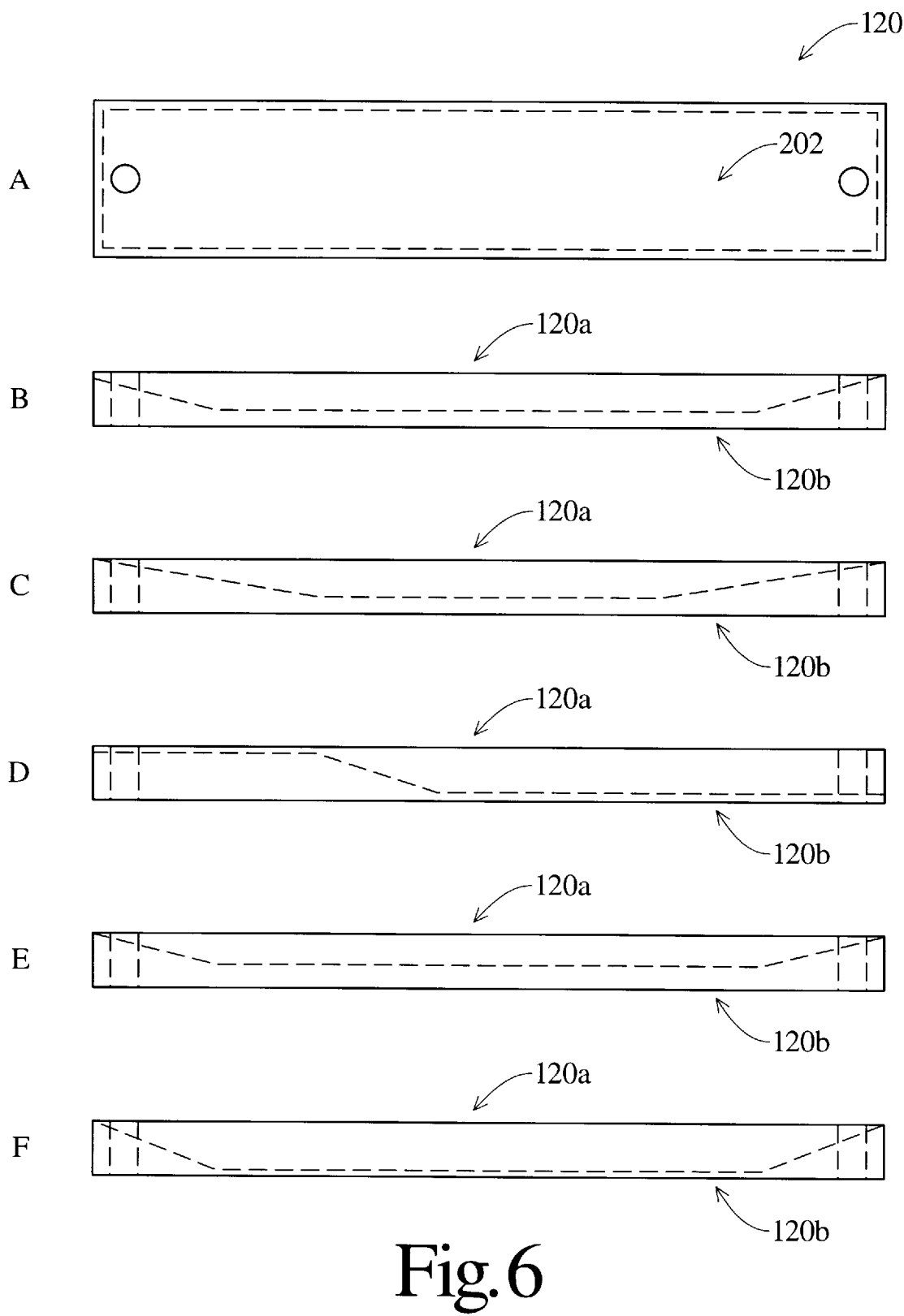
FIG. 6 depicts various beam shaping filters according to the present invention.

With reference to FIG. 6, the filter 120 comprises an aluminum substrate having a longitudinal channel 202. The length and width of the channel are sufficient to cover the outlet of the collimator 150. The depth of the channel is varied based on a desired attenuation profile. Stated conversely, the depth of the channel is varied so that the emitted transmission radiation has a desired intensity profile. The channel 202 contains a radiation attenuating material, for example a 90% tin, 10% antimony mixture. Of course, a shallower channel will provide relatively little attenuation, a deep channel will provide relatively more.

With reference to FIG. 6b, a filter adapted for imaging the torso attenuates the transmission radiation beam most strongly in the regions where the torso does not provide significant attenuation. In the preferred embodiment, the channel has a constant, relatively shallow depth in the area of the torso. The depth of the channel increases beginning near the edge of the torso, increasing to a maximum near the edge of the filter. FIG. 6c depicts a filter adapted for imaging the head. Again, the thickness of the tin-antimony layer, and thus the amount of radiation attenuation, is generally inversely related to the attenuation provided by the object being imaged.

The filter has been described with respect to a system where the line source is disposed orthogonally to the longitudinal axis 14. The beam shaping filter is of course applicable to other configurations, including for example, systems in which the transmission source is disposed parallel to the longitudinal axis and systems having a fan transmission beam geometry. A head filter suitable for use in such a system is depicted in FIG. 6d.

The intensity of the transmitting radiation can be varied by other means. For example, it will be appreciated that the degree of attenuation can be altered by varying the composition of the radiation attenuating material. Alternatively, the activity of radionuclide source can be varied to produce a desired intensity profile.

As yet another alternative, the collimator slots may be blocked with shielding elements or pegs inserted at the outlet of the transmission source collimator 150. The pegs preferably comprise a radiation attenuation material such a tin or lead. The spacing of the pegs is varied such that the effective area of the collimator 150 output is varied according to the desired intensity profile. In the case of a torso filter, for example, the pegs are spaced increasingly closer together as one reaches the ends of the collimator. In this way, an intensity filter similar to those produced by the filters shown in FIGS. 6b–6f can be produced. Of course, other intensity profiles can readily be achieved.

A family of filters having varying channel depths for each of the profiles is desirable. For example, the minimum thickness of the radiation absorbing material in one of the filters may be of an appropriate thickness to absorb about half of the transmission radiation from the radiation source. Another of the filters might have a thinner minimum thickness of the tin-antimony portion such that only about ¼ of the radiation is absorbed. Another one might only absorb 1/10 of the radiation, and so on. As the radiation source decays, the filters are replaced with filters which attenuate a progressively smaller percent of the radiation. In this manner, the output from the transmission line source assembly can be kept substantially constant over two or more half-lives of the radioisotope in the transmission radiation source. Examples of varying minimum thickness for a torso filter profile are depicted in FIGS. 6b, 6e, and 6f.

Each filter is preferably provided with distinctive colored markings to aid in identifying and selecting the appropriate filter. The selected filter is entered using operator interface 77 so that correct attenuation factors can be calculated based on the filter profile. Automatic coding of the filters, for example by electrical or optical coding, can be implemented so that appropriate attenuation factors are automatically determined.

Finally, it should be noted that more than one scanning line source may be installed on a given system. Each detector head is thus fitted with a line source as described above such that each detector head receives transmission radiation from an opposed transmission source.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A nuclear camera system comprising:
    a gantry disposed about an examination region;
    a first detector head mounted to the gantry, the first detector head having a radiation sensitive face facing toward the examination region;
    a second detector head mounted to the gantry opposite the first detector head, the second detector head having a radiation sensitive face facing toward the examination region;
    a first transmission radiation source movably mounted between the radiation sensitive face of the first detector head and the examination region, the first transmission radiation source comprising a source housing, a radionuclide source, and a source holder for holding the radionuclide source, the source holder being rotatably mounted within the source housing;
    means for moving the first transmission radiation source across the first detector head, whereby the second detector is irradiated by transmission radiation from the first transmission radiation source.

2. The system of claim 1 wherein the source holder has an axis of rotation and the radionuclide source is offset therefrom.

3. The system of claim 1 wherein the radionuclide source is offset from the center of the source holder.

4. The system of claim 3 wherein the source holder comprises bronze.

5. The system of claim 1 further comprising means for disposing the radionuclide source in an open position, a closed position, and an access position.

6. The system of claim 1 further comprising a second transmission radiation source movably mounted between the radiation sensitive face of the second detector head and the examination region;
    means for moving the second transmission radiation source across the detector head,
    whereby the first detector head is selectively irradiated by transmission radiation from the second transmission radiation source.

7. The system of claim 1 wherein the first and second detector heads are rotatable about the examination region.

8. The system of claim 1 wherein the first detector head further comprises a collimator and the transmission radiation source is disposed between the collimator and the examination region.

9. The system of claim 1 further comprising means for varying the intensity of the transmission radiation according to a desired intensity profile.

10. A nuclear camera system comprising:
    a gantry disposed about an examination region;
    at least a first nuclear camera detector head mounted to the gantry, said first detector head comprising a detector which faces the examination region;
    a transmission radiation source assembly for emitting transmission radiation which traverses the examination region and which is detectable by the first detector, the source assembly comprising:
    a source housing;
    a radionuclide source retained within the source housing;
    means for rotating the radionuclide source to an open position, a closed position, and an access position.

11. The system of claim 10 wherein the source assembly is mounted in a position in relation to the gantry, and further comprising means for preventing removal of the source assembly from said position in relation to the gantry depending on the position of the radionuclide source such that the source assembly is selectively removable from said position in relation to the gantry.

12. The system of claim 10 wherein the transmission radiation source further comprises a radiation source holder rotatably mounted within the source housing, the radionuclide source being retained near the periphery of the source holder.

13. The system of claim 12 wherein the source holder comprises a longitudinal groove for receiving the radionuclide source and means for retaining the radionuclide source in the groove.

14. The system of claim 12 wherein the source holder comprises bronze.

15. The system of claim 10 further comprising filter means for varying the intensity of the transmitted radiation in a manner generally inverse to the attenuation profile of an object being imaged.

16. A nuclear camera system comprising:
    a gantry disposed about an examination region:
    a first nuclear camera detector head mounted to the gantry, said first detector head comprising a detector which faces the examination region;
    a second detector head mounted to the gantry opposite the first detector head, said second detector head comprising a detector which faces the examination region;
    a transmission radiation source assembly for emitting transmission radiation which traverses the examination region and which is detectable by the first detector, the source assembly comprising:
    a source housing;
    a radionuclide source retained within the source housing;
    means for disposing the radionuclide source in an open position, a closed position. and an access position;
    wherein the transmission radiation source is mounted (i) between the radiation sensitive face of the second detector head and the examination region; and (ii) across the examination region from the first detector head, the source being movable with respect to the first detector head, whereby the first detector is selectively irradiated by transmission radiation from the transmission radiation source.

17. A gamma camera system comprising:
    a gantry disposed about an examination region, the examination region having a longitudinal axis;
    at least a first detector head mounted to the gantry, the first detector head having a detector comprising a radiation sensitive face facing toward the examination region;
    a transmission radiation source for emitting transmission radiation which traverses the examination region and which is detectable by the first detector head;
    means for varying the intensity of the transmission radiation according to a desired intensity profile in a direction parallel to the longitudinal axis.

18. The system of claim 17 wherein the intensity of the transmission radiation is generally related to the attenuating characteristics of an object situated in the examination region such that the intensity of the transmission radiation is relatively lower in at least a region where the object does not substantially attenuate the transmission radiation.

19. The system of claim 17 wherein the transmission radiation source assembly is movable in a direction orthogonal to the longitudinal axis, whereby at least a portion of the detector may be selectively irradiated with transmission radiation, the intensity of the transmission radiation varying in a direction perpendicular to the direction of motion.

20. The system of claim 17 wherein the means for varying comprises a filter disposed in the path of the transmission radiation and means for moving the transmission radiation source in a direction orthogonal to the longitudinal axis.

21. The system of claim 20 wherein the filter comprises a substrate;

a radiation attenuating material disposed on the substrate, the thickness of the radiation attenuating material being varied according to the desired intensity profile.

22. The system of claim 21 wherein the substrate comprises aluminum and the attenuating material comprises at least one of tin and antimony.

23. A method of diagnostic imaging comprising the steps of:

detecting radiation emitted by an object in the examination region of a nuclear camera, the examination region having a longitudinal axis;

transmitting radiation through at least a portion of the examination region using a transmission radiation source;

varying the intensity of the transmission radiation in a manner generally inverse to the attenuating characteristics of the object in a direction parallel to the longitudinal axis;

detecting the transmission radiation;

reconstructing an image representation from the radiation emitted by the object and correcting the image representation in accordance with the transmission radiation.

24. The method of claim 23 further comprising the step of moving the transmission source in a direction perpendicular to the longitudinal axis so as to selectively irradiate at least a portion of the examination region.

25. The method of claim 23 further comprising the step of varying the distance between the transmission radiation source and the detector.

26. The method of claim 23 further comprising the step of rotating the transmission radiation source about the examination region.

27. The method of claim 23 wherein the transmission radiation source is a line source.

28. A method of diagnostic imaging comprising the steps of detecting radiation emitted by an object in the examination region of a nuclear camera, the nuclear camera including a first and second detector mounted in an opposed relationship with respect to the examination region;

transmitting radiation through at least a portion of the examination region using a transmission radiation source disposed between the first detector and the object:

varying the intensity of the transmission radiation in a manner generally inverse to the attenuating characteristics of the object;

detecting the transmission radiation;

reconstructing an image representation from the radiation emitted by the object and correcting the image representation in accordance with the transmission radiation.

29. The method of claim 28 further comprising the steps of retaining a radionuclide line source near the periphery of a source holder, the source holder having a diameter;

rotating the source holder to an open position whereby transmission radiation is emitted in the direction of the second detector; and using substantially the entire diameter of the source holder to attenuate transmission radiation emitted in the direction of the first detector.

30. A method of replacing a nuclear camera radionuclide source, the radionuclide source being retained on a source holder rotatably mounted within a transmission radiation source assembly, the source holder being rotatable to at least an access and a closed position, the method comprising the steps of:

rotating the source holder to the closed position;

removing the transmission radiation source assembly from the nuclear camera said removal locking the source holder in the closed position;

moving the transmission radiation source assembly to a desired location;

unlocking the source holder;

rotating the source holder to the access position;

replacing the radionuclide source.

31. The method of claim 30 further comprising the step of locking the source holder in the access position, the source holder remaining mounted to the source assembly.

* * * * *